United States Patent
Tuli et al.

(10) Patent No.: US 6,242,257 B1
(45) Date of Patent: *Jun. 5, 2001

(54) TISSUE CULTURE PROCESS FOR PRODUCING A LARGE NUMBER OF VIABLE COTTON PLANTS IN VITRO

(75) Inventors: Rakesh Tuli; Alok Kumar Srivastava; Shiv Kumar Gupta, all of Lucknow (IN)

(73) Assignee: Council of Scientific & Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/862,004

(22) Filed: May 22, 1997

Related U.S. Application Data

(63) Continuation-in-part of application No. 08/792,546, filed on Jan. 31, 1997, now abandoned.

(30) Foreign Application Priority Data

Oct. 29, 1996 (IN) .................................................... 2334/96

(51) Int. Cl.⁷ ..................................................... C12N 5/02

(52) U.S. Cl. ........................ 435/427; 435/430; 435/430.1; 435/431

(58) Field of Search ..................................... 435/427, 430, 435/430.1, 431

(56) References Cited

PUBLICATIONS

Gould et al., 1991, Plant Cell Rep., 10:12–16.*
Bajaj et al, Indian J. of Exp. Biol., 24:581–583.*
Trolinder et al., 1987, Plant Cell Rep., 6:231–234.*
Dani et al., Advances in Plant Sciences 6 (2). 1993. 260–264.*

* cited by examiner

*Primary Examiner*—Irene Marx
(74) *Attorney, Agent, or Firm*—Fish & Neave; Margaret A. Pierri; Dutch D. Chung

(57) ABSTRACT

The present invention relates to a tissue culture process for producing a large number of viable cotton plants in vitro from a specified tissue of cotton plant. The invention provides genotype independent, direct, multiple shoot proliferation and opens up new possibilities for micropropagation, selection of mutants and for producing genetically improved cotton plants by modern methods of agrobiotechnology and genetic engineering. The protocol provides an important step in the success of cotton improvement programmed, utilizing tissue culture technology.

23 Claims, No Drawings

TISSUE CULTURE PROCESS FOR PRODUCING A LARGE NUMBER OF VIABLE COTTON PLANTS IN VITRO

CROSS-REFERENCE TO RELATED APPLICATIONS

This is a continuation-in-part of application Ser. No. 08/792,546, filed on Jan. 31, 1997 now abandoned, entitled "A Tissue Culture Process For Producing A Large Number of Viable Cotton Plants In Vitro".

FIELD OF THE INVENTION

The present invention relates to a tissue culture process for producing a large number of viable cotton plants in vitro from a specified tissue of cotton plant. The invention provides genotype independent, direct, multiple shoot proliferation and opens up new possibilities for micropropagation, selection of mutants and for producing genetically improved cotton plants by modern methods of agrobiotechnology and genetic engineering. The protocol provides an important step in the success of cotton improvement programmed, utilizing tissue culture technology.

BACKGROUND AND PRIOR ART REFERENCES

Cotton is a globally important crop, grown primarily for fiber. Seeds provide an important source of food for livestock. Cotton has influenced economic development of many nations, throughout the world. Therefore, cotton improvement programmes by modern methods of agrobiotechnology are of interest worldwide. This has increased the importance of developing tissue culture methods to facilitate the application of modern techniques of genetic engineering of cotton plant.

Several reports on tissue culture of cotton have been published. These are related to direct shoot differentiation and somatic embryogenesis through suspension and callus cultures. These are listed below by way of references.

Organogenesis and regeneration, leading to micropropagation by tissue culture methods have been successfully demonstrated in several plant species e.g. Phaseolus sp. (Rubluo A & Kartha K K 1985). In vitro culture of shoot apical meristems of various Phaseolus species and cultivars, J. of Plant Physiol 119: 425–433. *Glycine max* (Shetty K., Asano Y and Oosawa K 1992 Stimulation of in vitro shoot organogenesis in *Glycine max* Merrill by allantoin and amides. Plant Sci. 81:245–252). *Cajanus cajan*(Shiv Prakash N, Pental D & Bhalla-Sarin N 1994 Regeneration of Pidgeonpea (*Cajanus cajan*) from cotyledonary node via multiple shoot formation. Plant Cell Rep. 13:623–622), Carnation (Claire Annex A. Yancheva S and Dons H 1995. Cells within the nodal region of carnation shoots exhibit a high potential for adventitious shoot formation. (Plant Cell Tiss. Org. Cult. 40:151–157) etc.

Plant regeneration by tissue culture techniques is well established. A wide variety of plant species has been successfully regenerated in vitro via organogenesis or somatic embryogenesis. Organogenesis leads to organ formation i.e., shoot (or root), which can be isolated to induce development of roots (or shoots) to produce full plant while somatic embryogenesis leads to the development of somatic embryos (embryos developed without fertilization) which have both shoot and root initials and are capable of developing into whole plant. Although the ability of individual parts of plants and cells to regenerate into complete plants (called totipotency) is a well known phenomenon, each plant or plant part requires specialized studies to invent the conditions that allow such regeneration. Some of the broadly applicable factors controlling growth and differentiation of such cultures have been determined. The establishment of interactions among different groups of phytohormones and growth regulators alone or in combinations are responsible for certain interrelations existing among cells, tissues and organs. There seems to be consensus that the success in inducing differentiation depends upon the type of explant, physiological condition of the explant and physical and chemical milieu of the explant during culture. Due to this, the science of tissue culture has been directed to optimize the physiological conditions of source plant, the type of explant, the culture conditions and the phytohormones used to initiate tissue culture. This substantiates the fact that development of a new process for proliferation of plants by tissue culture is not obvious.

One major aspect that has to be investigated on case to case basis is the type of plant growth regulators and the amount of plant growth regulators that induce regeneration. Besides chemical composition of the medium, temperature of growth and other culture conditions play important role in the induction of organogenesis and somatic embryogenesis and maturation of shoots and roots and the formation of healthy fertile plants. The response to medium, hormones and growth conditions differs from plant species to species and variety to variety. Thus, inventing conditions for efficient regeneration of plants, organogenesis and somatic embryogenesis requires developing specialized knowledge about a given plant.

Another major area where innovativeness is required in tissue culture is identifying the plant part that efficiently responds to the culture conditions and leads to prolific regeneration. Not all plant parts of a given species are amenable to efficient regeneration. It is a complex combination of the plant part identified for totipotency (called explant), the physiological state of the explant and the growth conditions, especially the growth regulators that determine success of a plant in tissue culture. Different explants from a given plant usually show very different response to growth conditions for proliferation. No general principles can be applied to achieve regeneration. In each case, identification of the explant and identification of the culture conditions are innovative steps in the development of a tissue culture method for regeneration of a plant part into a number of plants or somatic embryos.

As of now, a detailed publication on the formation of multiple shoots from any tissue explant of cultivated varieties of cotton is not available. This invention describes for the first time a detailed protocol for organogenesis from a small part (called an explant) of cotton seedling to give multiple shoots of cotton plant through tissue culture. The method is very useful in agricultural biotechnology for micropropagation and genetic transformation because it shows wide applicability to all the cultivars tested by the inventors and the shoots can be efficiently raised to maturity. The method has a great potential in cotton improvement programmes by modern methods of agrobiotechnology.

Several reports deal with tissue culture conditions (Davidonis G H and Hamilton R H, 1983 Plant regeneration from callus tissue of *Gossypium hirsutum* L. Plant Sci. Lett. 32: 89–93; Shoemaker R C, Couche L J & Galbraith D W 1986). Characterization of somatic embryogenesis and plant regeneration in cotton (*Gossipium hirsutum* L) Plant Cell Rep. 3:178–181; Trolinder N L and Goodin J R 1987; Somatic embryogenesis and plant regeneration in cotton Gossipium hirsutum L. Plant Cell Rep. 6:231–234 Finer J. 1988). Plant regeneration from somatic embryogenesis suspension cultures of cotton Gossipium hirsutum. (Plant Cell Rep. 7:399–402) that give rise to somatic embryos (structures that give rise to normal plants without going through fertilization) have been reported. Initiation and maturation of somatic embryos take several months. The method is highly dependent on genotypes (Trolinder N L and Xhixian C., 1989 Genotype specificity of the somatic embryogenesis response in cotton. Plant Cell Rep. 8:133–136) and is, therefore, applicable to a restricted group of varieties. Initiation and maturation of somatic embryos takes several months, and the plants regenerated via somatic embryogenesis were of ten reported to be cytologically and morphologically abnormal (Stelly D M, Altman D W, Kohel Rz, Rangan T S & Commeskey E 1989. Cytogenetic abnormalities of cotton somaclones from callus cultures. (Genome 32:762–770). Plants developed via somatic embryogenesis were also of ten reported to be sterile (Trolinder N L & Goodin J R 1987, Somatic embryogenesis and plant regeneration in cotton Gossipium hirsutum L. Plant Cell Rep. 6:231–234).

These regeneration processes have been successfully used in Agrobacterium mediated gene transfer in cotton (Umbeck P, Johnson G, Barton K. Swain W 1987 "Genetically transformed cotton Gossipium hirsutum L. Plant Bio./ Technology 5:263–266; Firoozabady E., DeBoer L D, Merlo J D, Halk L E, Amerson, N L, Rashka K E and Murrey E E 1987. Transformation of cotton Gossypium hirsutum L. by Agrobacterium tumefaciens and regeneration of transgenic plants. Plant Mol. Biol. 10:105116) and in particle bombardment procedure (Finer J J and McMullen M 1990, Transformation of cotton Gossypium hirsutum L. via particle bombardment Plant Cell Rep. 8:586–589). Certain bacterial genes, like those encoding herbicide resistance (Bayley C, Trolinder N L, Ray C, Morgan M, Quisenberry J E and OW DW 1992, Engineering 2.4-D resistance into cotton (Theo. Appl. Genet. 83:45–649) and Bacillus thuringiensis endotoxin genes (Perlak F J, Deaton R W, Armstrong T A, Fuchs R L Sims S R, Greenplate J T & Fischhoff D A 1990. Insect resistant cotton plants. Bio/Technology 8:939–943) have been successfully expressed in transgenic cotton plants. But these advances are presently restricted only to Coker cultivars of cotton because other cultivars did not respond to the above mentioned tissue culture i.e., somatic embryogenesis protocols.

There have been publications describing in vitro development of a single shoot from a shoot apex tissue of cotton plant under aseptic tissue culture conditions (Gould J., Banister S, Hassegawa O, Fahima M, Smith R H 1991. Regeneration of Gossypium hirsutum and G. barbadense from shoot apex tissue for transformation. Plant Cell Rep. 10:12–16). Apical meristems and shoot tips of cotton plants have been used for culture to obtain callus, adventitious buds and multiple shoots (Bajaj Y P S and Manjeet Gill 1986: Preservation of cotton Gossypium sps. through shoot tip and meristem culture (Indian J. of Exp. Biol. 24:581–583). In these reports, the response of the cultures was genotype dependent and rooting was very infrequent. Due to this problem, the reproducibility of these processes was not very good.

Recently, (McCabe D E and Martinelli B J 1993, Transformation of elite cotton cultivars via particle bombardment of meristems Bio/Technology 11:596–598; Chlan C A, Lin J, Cary J W & Cleveland T E 1995, A procedure for biolistic transformation and regeneration of transgenic cotton from meristematic tissue (Plant Mol. Bio. Rep. 13:31–37) cotton embryonic axes were used for introducing genes by biolistic transformation method. In these reports, a single apical meristem grew into a single shoot. The regenerated shoots were then rooted on suitable medium to obtain mature plants of cotton. In all such reports, transformation and regeneration were inefficient since a single apical meristem developed into a single mature plant and most of the transformants were chimeric with respect to the expression of transformed genes. Such process can be largely improved by developing a process wherein many plants develop from single explant, as disclosed in this invention.

Table 1 summarises the state of art of tissue culture process related to cotton plant as covered by patents or described in literature. It is then followed by a statement describing the process invented by us in contrast to the known state of art.

The abbreviations used in the text for the plant growth regulators (hormones) employed in the culture medium are: BAP (6-benzyl amino purine or 6-benzyl adenine), 2iP (γγdimethyl allylamino purine), Kin (kinetin), IAA (indole acetic acid), NAA (naphthalene acetic acid), IBA (indole butyric acid), TDZ (1-phenyl-3, 1.2.3 thidiazol-5-yl urea), DU (diphenyl urea), PU (U-1-phenyl N 4 pyridyl urea) and 2.4D (2.4 diphenoxy acetic acid).

TABLE 1

State of art for tissue culture regeneration in cotton.

| | Report | Mode of regeneration | Phytohormones | Explant | Remarks |
|---|---|---|---|---|---|
| 1. | Davidonis GH and Hamilton RH (1983) Plant Regeneration from callus tissue of G. hirsutum L. Plant Sci. Lett. 32:89–93 | Somatic embryogenesis | NAA and Kinetin | Cotyledon | 2 year old calli of G. hirsutum L. cv. Coker 310 grown on LS medium containing 30 gm/L glucose in abscence of NAA and kin were used. 30% cultures gave rise to somatic embryos. |
| 2. | Davidonis GH, Mumma RO, Hamilton RH, 1987 controlled regeneration of cotton plants from tissue culture U.S. Pat. No. 4672035 | --do-- | --do-- | --do-- | --do-- |
| 3. | Shoemaker RC, Couche LS, and Galbraith DW 1986, characterization of somatic embryogenesis and plant regeneration in cotton Gossypium | Somatic embryogenesis | NAA, Kinetin | Hypocotyl | 17 cultivars of cotton G. hirsutum L. were evaluated for somatic embryogenesis. After a series of transfer of calli through medium containing MS salts, NAA & kin. |

TABLE 1-continued

State of art for tissue culture regeneration in cotton.

| | Report | Mode of regeneration | Phytohormones | Explant | Remarks |
|---|---|---|---|---|---|
| | *hirsutum* L. Plant Cell Rep. 3:178–181 | | | | After several weeks calli were observed for the presence of somatic embryos. Cultivars Coker 201 and Coker 315 were identified as embryogenic. The embryos were isolated and developed into plants. |
| 4. | Trolinder NL, and Goodin JR 1987, somatic embryogenesis and Plant regeneration in cotton *Gossypium hirsutum* L. Plant Cell Rep 6:231–234 | Somatic embryogenesis | 2,4-D, Kin | Hypocotyl | Globular Embryos were observed in 6-week-old callus culture. At this stage calli were subcultured to liquid suspension in growth regulator free medium. After 3–4 weeks suspensions were sieved to collect globular and heart stage embryos. Collected embryos were developed on solidified medium to maturity. Mature embryos were germinated into plants. Most of the plants developed by this method were sterile (only 15% of the plants were fertile). |
| 5. | Trolinder NL and Xhixian C 1989, Genotype specificity of the somatic embryogenesis response in cotton. Plant Cell Rep. 8:133–136 | Somatic embryogenesis | 2,4-D & Kin | Hypocotyl | 38 cultivars, strains and races of Gossypium were screened for somatic embryogenesis with the method developed for Coker 312. Screening indicated that genotype variation for embryogenesis existed. Only a few genotype are amenable to the model developed for Coker 312. |
| 6. | Stelly DM, Altman DW, Kohel RZ, Rangan TS and Commeskey E 1989, cytogenetic abnormalities of cotton cultures. Genome 32:762–770 | | | | A high frequency of chromosomal anomaly was observed in plants regenerated through somatic embryogenesis and most of the plants regenerated through somatic embryogenesis were sterile. |
| 7. | Finer J 1988, Plant Regeneration from somatic embryogenesis suspension cultures of cotton *Gossypium hirsutum* Plant Cell Rep 7:399–402. | Somatic embryogensis | NAA, Kin Picloram,2,4-D | Cotyledon | Maintainable embryogenic suspension cultures were developed. Embryos were developed by transferring embryogeneic tissue to auxin free medium. Plants derived were fertile. |
| 8. | Finer J, 1990. An efficient method for regenerating cotton from cultured cells. Patent No. ZA/A8808599 | --do-- | --do-- | --do-- | --do-- |
| 9. | Rangan TS: 1993 Regeneration of cotton Patent No. 5244802 | Somatic embryogenesis | NAA, Kin | Hypocotyl, Cotyledon, Immature embryo | Callus was initiated on MS medium containing NAA & kin, subcultured every $3^{rd}$ week for growth. Somatic embryos were formed four to six months after placing tissue on callus initiation medium. Many varieties were identified as embryogenic in vitro are SJ2, SJ4, SJ5, SJ2C, GC510, B1644, B2710, Siokra and FC 2017. |
| 10. | Gawel NJ and Robacker CD 1990 somatic embryogenesis in two *Gossypium hirsutum* genotypes on semisolid vs liquid proliferation media. Plant Cell Tissue Organ Culture 23:201–204 | Somatic embryogenesis | 2,4D & kin | Petiole from mature flowering plants | A comparative study was made for somatic embryogenesis in liquid vs solid media & it was found that culture on liquid media favors the somatic embryogenesis in both the genotypes named Coker 312 & T-25. |
| 11. | Bajaj YPS and Gill M, 1986 Preservation of cotton Gossypium sps through shoot tip and meristem culture. Indian J. of Exp. Biol. 24:581–583 | Callus culture Adventitious bud culture & multiple shoot | NAA, IAA, kin | Shoot tip | Response of culture was genotype dependent and only a few cultures gave multiple shoots while rooting was also very infrequent. |
| 12. | Gould J, Banister S, Hassegawa O, Fahima M., Smith RH 1991. Regeneration of *Gossypium hirsutum* and *G. barbedense* from shoot apex tissue for transformation. Plant Cell Rep. 10:12–16 | Organogenesis from pre-existing meristems | Nil | Apical shoot meristem | Normal and fertile plants of *G. barbedense* Pima S-6 and 19 cultivars of *G. hirsutum* were regenerated using this method but only one shoot is formed from one explant & rooting could not be optimised. |

TABLE 1-continued

State of art for tissue culture regeneration in cotton.

| | Report | Mode of regeneration | Phytohormones | Explant | Remarks |
|---|---|---|---|---|---|
| 13. | Umback P, Johnson G, Barton K, Swain W, 1987 genetically transformed cotton (*Gossypium hirsutum* L). Plant. Biotechnology 5:263–266 | Genetic transformation of cotton & regeneration of plants | 2,4-D,Kinetin | Hypocotyl | Method of genetic transformation of cotton was disclosed. Immature tissue of cotton was transformed in vitro by *Agrobacterium tumefaciens* mediated genetic transformation method. The resulting cotton tissues were screened for transformation by selection on drug. Transformed cultures were then induced to give somatic embryos. The somatic embryos were developed into mature plants. Coker 310, 312 & 5110 were transformed by this method. |
| 14. | Umback P, 1991 Method of producing transformed cotton cells by tissue culture, Patent No. IN A 168950 | | | | |
| 15. | Firoozabady E. DeBoer LD, Merlo JD, Halk LE, Amerson NL, Rashka KE and Murrey EE 1987, Transformation of cotton *Gossypium hirsutum* L. by *Agrobacterium tumefaciens* and regeneration of transgenic plants. Plant Mol. Bio. 10:105–116 | Genetic Transformation & regeneration of transgenic plants | 2iP, NAA | Cotyledon | Cotyledon explants from 12 day old seedlings were transformed and plants were regenerated. For regeneration the explant treated with *Agrobacterium tumefacines* were transferred to medium containing bacteriostatic & selective agents so that only transformed cells give rise to callus. Callus when subcultured to hormone free medium gave rise to transgenic plants. Using this method *G. hirsutum* Coker 201 was transformed. |
| 16. | Perlak FJ, Deaton RW, Armstrong TA, Fuchs RL, Sims SR, Greenplate & Fischoff DA 1990. Insect resistant cotton Plants Bio/Technology 8:939–943 | Transformation & regeneration of Transgenic Plants (via somatic embryogenesis | 2,4-D, Kinetin | Hypocotyl | Truncated forms of the insect control protein genes of *Bacillus thuringiensis* var. Kurstaki HD-1 (cry 1A(b) and HD73 CrylA(c)) were transformed into cotton hypocotyl section via *Agrobacterium tumefaciens* and somatic embryos were obtained from transformed cells and finally insect resistant cotton plants of *G. hirsutum* cv. Coker 312 were obtained. |
| 17. | Baylay C, Trolinder NL, Ray C, Morgan M, Quisenberry JE and OwDW 1992. Engineering 2,4-D resistance into cotton. Theo. Appl. Genet. 83:645–649 | Transformation & regeneration (via somatic embryogenesis of transgenetic plants) | 2,4-D, Kinetin | Hypocotyl | 2,4-D monooxygenase gene tfd A from *Alcaligenus eutrophus* was isolated, modified and expressed in tobacco and cotton plants transformation was done by *Agrobacterium tumefaciens* and 2,4D resistant plants of Coker 312 line were obtained. |
| 18. | Rangan T, Rajsekran, Hudspeth and Yenofsky (1989) Regeneration and transformation of cotton Patent No. EP344302 | Transformation and regeneration (via somatic embryogenesis) of transgenic plants. | NAA, Kinetin | Hypocotyl, cotyledon, Immature embryo | Regeneration and transformation of cotton (*G. hirsutum* var. Acala SJ2, SJ4, SJ5, SJ2-1, GC510, B1644, B2724, B1810, Picker Variety of Siokra & stipper var FC2017) transformation was done by *Agrobacterium tumefaciens* somatic embryos obtained from callus were germinated on Beasley and Ting's medium. |
| 19. | Finner JJ and Mc Mullen (1990) Transformation of cotton *Gossypium hirsutum* L. via particle bombardment Plant Cell Rep. 8:586–589 | Transformation & regeneration (via somatic embryogenesis) of transgenic plants | NAA, kin, 2,4D picloram | Cotyledonary leaf disc | Embryogenic suspension cultures of cotton were subjected to particle bombardment where high density particles carrying plasmid DNA were accelerated towards the embryogenic plant cell. These cells were then subjected to developmental process of somatic embryo in the presence of selection agent (Hygromycin) cv. Coker 310 was transformed by this method. |
| 20. | McCabe DE and Martinelli BJ (1993) Transformation of Elite cotton cultivars via particle bombardment of meristems Bio/Technology 11:596–598 | Organogenesis from pre-existing meristems | BA (a brief treatment for 15 hrs) | embryonic axes | The process involves excising the embryonic axes from germinating seeds and blasting particles carrying foreign genes into the embryonic axes. From the treated embryonic |

TABLE 1-continued

State of art for tissue culture regeneration in cotton.

| Report | Mode of regeneration | Phytohormones | Explant | Remarks |
|---|---|---|---|---|
| | | | | axes, plants were developed and screening was done for transformed plants. Only one plant develop from a single axes. Using this method, the following cotton cultivars are transformed. Pima, sea Island cotton and upland varities. |
| 21. McCabe DE and Martineli BJ (1992) Particle mediated transformation of cotton. Patent No. PCT/US92/0172 | --do-- | --do-- | --do-- | --do-- |
| 22. Chlan CA, Lin J, Carry JW & Cleveland TE, 1995. A procedure for biolistic transformation and regeneration of transgenic cotton from meristematic tissue. Plant Mol. Bio. Rep. 13:31–37 | Organogenesis from pre-existing meristems | BA, IAA | Embryonic axes | Embryonic axes were aseptically removed and bombarded with DNA coated 1.6 A° gold particle at a repture pressure 90 or 110 kg/cm$^2$. After bombardment, these tissues were grown in to whole plant in the presence of kannamycin selection. Single axis gave only on plant. |

NOVELTIES INVOLVED IN THE PRESENT INVENTION VIS A VIS PRIOR ART

The present invention provides for the first time an efficient process that results in the development of new meristematic zones in an apical explant from cotton seedlings and gives rise to a large number of shoots. Further, the explant forms an organogenic mass at the base which can be divided into smaller parts to achieve sustained cycles of multiple shoot regeneration repeatedly and reproducibly. The process of this invention is very simple and is applicable to a wide range of varieties and species of Gossypium. It is by and large genotype independent, rapid and convenient for applications in micropropagation and genetic transformation.

The process of the present invention employs a starting material (explant) different from those used in earlier reports, gives a true to original plants because it is based on direct organogenesis, takes shorter time, is simple and gives large number of fertile and normal plants. The reports and the patents in Table 1 are highly variety (genotype) dependent. The process described by the applicants is applicable to a large number of varieties of different species. The reports 20 and 22 of Table 1 and the patented claims 21 in Table 1 use embryonic axis as the explant and the process leads to formation of a single shoot rather than several shoots as described by the applicants. The reports 4 and 6 of Table 1 gives rise to sterile plants while the present process described in this application gives healthy plants which are fertile.

The success of the present invented process depends upon the age of the seedling and the manner in which the explant is removed from the seedlings for culturing by the process of this invention. In the present invention, cotyledonary node (also called Cotyledonary axil or apical meristem of seedling) is taken out of the seedlings 2–20 days old. Depending upon the variety, variable number of shoots are obtained following culture of the explant removed from such seedlings. Apical meristem taken without cotyledonary leaves or taken along with one or part of cotyledonary leaf and 0.5 cm of hypocotyl gave multiple shoots. The process gave a large number of shoots in one step from apical meristem taken without cotyledonary leaves. The requirement for growth regulators was different depending upon the explant. When apical meristem was taken without cotyledonary leaves, multiple shoot proliferation required both BAP and kinetin. On the other hand, when one or part of one cotyledon was included, multiple shoot regeneration required BAP alone. The hormone combinations used by us and the explant are quite different from those used in any of the reports described in Table 1. The multiple shoot regeneration in our protocol was successful within certain limits of the hormone levels. For example, BAP functions efficiently at concentration of 10 to 100 $\mu$M to give shoots from apical axil in the presence of one or part of one cotyledonary leaf. Cotyledonary axil alone works efficiently in presence of BAP at concentrations of 4 to 20 $\mu$M along with kinetin at concentrations of 2 to 20 $\mu$M. As described in Table 1 these growth regulators, i.e., BAP in combination with kinetin have not been used earlier for the development of a process for multiple shoot regeneration in cotton. In earlier reports 11 and 12 in Table 1, their processes gave rise to poor roots, whereas the process of the present invention is superior in that respect.

The process of inducing multiple shoot development involves cells other than original meristems which naturally grow to develop single plant. We have identified an explant which gives new meristems resulting in multiple shoots when cultured on medium supplemented with suitable concentration of commonly used growth regulators. The technique can be applied to any variety, cultivar, strain or race of cotton. The process is a novel approach and is free of genotypic limitation and also reduces the time required for regeneration which are serious problems in the prior art.

The present invention provides for the first time an efficient process that results in the development of new meristematic zones in an apical explant from cotton seedling and gives rise to several shoots. Further, the explant forms an organogenic mass at the base which can be divided into smaller parts to achieve sustained cycles of multiple shoot regeneration repeatedly and reproducibly.

The earlier patents in the related area on cotton are U.S. Pat. Nos. 4672035 and 5244802 wherein the inventors disclosed processes for regeneration of plants from cotton callus in Gossypium hirsutum L. cv. Coker 310 via somatic embryogenesis; U.S. Pat. No. 8,693,7384 & CA Al, 1335799 wherein the inventors disclosed a process for regeneration and transformation of cotton involving the somatic embryogenesis based regeneration process and patent WO A1 9215675 wherein the inventor disclosed a method for bombardment mediated transformation of cotton embryos wherefrom the transgenic plants were developed.

The process described in this invention does not aim at somatic embryogenesis. The present process is very simple to adopt commercially and is applicable to a wide range of varieties and species of Gossypium. It is by and large genotype independent, rapid and convenient for applications in micropropagation and genetic transformation. Unlike state of art technologies, this process does not lead to the formation of plants with morphological and cytogenetic abnormalities.

The process of the present invention employs a starting material (explant) different from those used in earlier reports, gives true to original plants because it is based on direct organogenesis, takes shorter time, is simple and gives fertile and normal plants.

OBJECTS OF THE INVENTION

The main objective of the present invention is to provide an improved process for efficient organogenesis in cotton cultivars with and sustained regeneration of a large number of plants from a specified plant tissue.

Another objective of the present invention is to provide an improved process for the renegeration of shoots of cotton plants in such a manner that these grow, develop roots easily and efficiently to form mature, fertile cotton plants.

Yet another objective of the present invention is to provide an improved process for the organogenic tissue culture of cotton plants that would be amenable in genetic transformation using Agrobacterium of DNA coated microprojectiles for delivery of DNA into plant cells.

Still another object of the present invention is to provide a process for development of disease-free cotton plants for exchange and conservation of disease-free germplasm.

To meet the above objects, the applicants have now provided a method for regenerating a large number of viable and fertile cotton plants by tissue culture technique starting from a cotyledonary node (also called cotyledonary axil or axis) with or without one or part of the cotyledonary leaf of cotton seedling, said method comprising:

(i) treating the seed of cotton plant to remove bacteria/fungus (contaminants) by conventional methods, (ii) culturing the treated seeds from step (i) for germination in a first medium consisting of:
    a. Salts of any conventional medium,
    b. Vitamins of any conventional medium,
    c. Carbon source, and
    d. Gelling Agent at a pH in the range of 5.4 to 6.2 and sterilizing the medium by autoclaving, the culturing was effected at the temperature 20–40° C. in the presence of light (at least 40$\mu$mol/m$^2$s) and 16 h photoperiod for a period of 3 days to several weeks, (iii) cutting cotyledonary node (explant) with or without one or a part of one complete cotyledonary leaf from the seedlings obtained in step (ii), (iv) culturing the explant obtained from step (iii) for the purpose of shoot proliferation in a second medium consisting of :
    a. Salts of any conventional medium,
    b. Vitamins of any conventional medium,
    c. Carbon source,
    d. Phytohormones (plant growth regulators) taken singly or in combination of cytokinins such as 6-benzyl amino purine, 6-benzyladenine, γγdimethyl allyl aminopurine, kinetin, 1-phenyl-3-(1,2,3-thidiazol-5-yl urea at a concentration in the range of 0.1 to 100 $\mu$M,
    e. Gelling Agent at a pH in the range of 5.4 to 6.2 and sterilizing the medium by autoclaving, the culturing was effected at a temperature in the range of 20–40° C. in light (40 $\mu$mol/m$^2$s) with 16 h photoperiod;

(v) continuing the culturing for a minimum period of 4 weeks till many shoots are formed;

(vi) harvesting the shoots formed;

(vii) transferring the harvested shoots to a root inducing medium (third medium) comprising:
    a. Salts of any conventional medium,
    b. Vitamins of any conventional medium,
    c. Carbon source,
    d. Phytohormones (plant growth regulators) comprising auxins selected from indole acetic acid, indole butyric acid and naphthalene acetic acid,
    e. Gelling Agent at a pH in the range of 5.4 to 6.2 and sterilizing the medium by autoclaving, and (viii) culturing the shoots at temperature 20–40° C. and light (40 $\mu$mol/m$^2$s) with 16 h photoperiod till roots are formed.

The preferred feature of the invention employs the first, second and third medium comprising salts of MS medium, vitamins of B5 medium, carbon source and gelling agent. However, the second and third medium, in addition, comprising phytohormones (plant growth regulators) and gelling agents. The most preferred salts of MS medium employed in the first, second and third medium comprise the following:

| Component | Concentration (mg/L) |
|---|---|
| a. Salts of MS medium: | |
| $NH_4NO_3$ | 1650 |
| $KNO_3$ | 1900 |
| $MgSO_4 7H_2O$ | 370 |
| $MnSO_4 H_2O$ | 169 |
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100 |

The preferred vitamins of the first, second and third medium are selected from:

| Components | Concentraion (mg/L) |
|---|---|
| Nicotinic acid | 1.0 |
| Pyridoxine HCl | 1.0 |
| Thiamine HCl | 10.0 |

The preferred carbon source used in the first, second and third medium is selected from sucrose or glucose and such carbon source employed is at a range of 1 to 6% wt/vol.

The phytohormones employed in the second medium are selected from cytokinins and cytokinin active urea or a combination thereof. Preferably, the phytohormones employed in the second medium are selected from cytokinins such as 6-benzyl amino purine, 6-benzyladenine, zeatin, (γγdimethyl allylamino purine), kinetin; and cytokinin active urea such as 1-phenyl-3-1,2,3 thidiazol-5-yl urea and diphenyl urea, 4-1-phenyl N(pyridyl) urea. The growth regulators used in the third medium are auxins such as indole acetic acid, naphthalene acetic acid and indole butyric acid.

The cotyledonary node (explant) is isolated from the germinated seedling 2 days to several weeks old and the explant used is taken from the cotton plant grown in field or by tissue culture. The basal regenerating tissue (remaining after shoots are harvested in the first cycle) is cultured repeatedly through steps (iv) to (viii) for sustained regeneration of plantlets. The concentration of salts of MS medium used are in full quantity as indicated earlier or at half the level on weight by volume basis. The gelling agents used are selected from agar gelrite (phytagel) or any gelling agent at the concentration varying from 0.2 to 1.2% w/v.

In addition, the shoots regenerated by the present tissue culture method can be used for micropropagation of cotton plant. Moreover, cotyledonary node or basal regenerating tissue produced by the present method can be used for genetic transformation based on Agrobacterium or via bombardment of DNA coated particles. Further, the shoots regenerated by the said tissue culture process can be used for production of disease free cotton plant or such shoots can be used for exchange and conservation of disease free cotton germplasm.

The most preferred method of the invention comprising:
(i) treating the seeds of cotton plant to remove the contaminants such as bacteria/fungus by conventional methods;
(ii) culturing the treated seeds for germination in a medium shown in Table 2.

TABLE 2

| Component | Concentration (mg/L) |
| --- | --- |
| A. Salts of MS medium: | |
| $NH_4NO_3$ | 1650 |
| $KNO_3$ | 1900 |
| $MgSO_4 7H_2O$ | 370 |
| $MnSO_4 H_2O$ | 169 |
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100 |
| B. Vitamins of B5 medium: | |
| Nicotinic acid | 1.0 |
| Pyridoxine HCl | 1.0 |
| Thiamine HCl | 10.0 |
| C. Carbon source: | |
| Sucrose/Glucose | 30000.0 |
| D. Gelling Agents | 0.2 to 1.2% w/v. | at a pH in the range of 5.4 to 6.2 and sterilizing the medium by autoclaving,
(iii) cutting the cotyledonary node (explant) along with cotyledonary axil from the seedlings obtained in step (ii)
(iv) culturing the explant obtained in step (iii) in a medium as shown in Table 3.

TABLE 3

| Component | Concentration (mg/L) |
| --- | --- |
| A. Salts of MS medium: | |
| $NH_4NO_3$ | 1650 |
| $KNO_3$ | 1900 |
| $MgSO_4 7H_2O$ | 370 |
| $MnSO_4 H_2O$ | 169 |
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100 |
| B. Vitamins of B5 medium: | |
| Nicotinic acid | 1.0 |
| Pyridoxine HCl | 1.0 |
| Thiamine HCl | 10.0 |
| C. Carbon source: | |
| Sucrose/Glucose | 30000.0 |
| D. Hormones (growth regulators) | |
| cytokinins | 0.1 to 100 µM |
| E. Gelling Agents | 0.2 to 1.2% w/v. | at a pH in the range of 5.4 to 6.2 and sterlizing the medium by autoclaving, (v) continuing the culturing at the temperature of 20 to 40° C. and light (40 µmol/m²s) 16 hrs. photoperiod for a period of 4 to 6 weeks or till many shoots are formed;
(vi) harvesting the shoots formed;
(viii) transferring the harvested shoots to a rooting medium as shown in Table 4.

TABLE 4

| Component | Concentration (mg/L) |
| --- | --- |
| A. Salts of MS medium: | |
| $NH_4NO_3$ | 1650 |
| $KNO_3$ | 1900 |
| $MgSO_4 7H_2O$ | 370 |
| $MnSO_4 H_2O$ | 169 |
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100 |
| B. Vitamins of B5 medium: | |
| Nicotinic acid | 1.00 |
| Pyridoxine HCl | 1.0 |
| Thiamine HCl | 10.00 |

TABLE 4-continued

| Component | Concentration (mg/L) |
| --- | --- |
| C. Carbon source: | |
| Sucrose/Glucose | 30000.00 |
| D. Hormones (growth regulators) | |
| Auxins | up to 50 μM |
| E. Gelling Agents | 0.2 to 1.2% w/v | at a pH in the range of 5.4 to 6.2 and sterlizing the medium by autoclaving, (viii) culturing the shoots at temperature 20 to 40° C. till roots are formed.

The plantlets so formed may be, if desired, transferred to the soil for growing cotton plants.

According to an embodiment of the invention, the success of the process depends upon the age of the seedling and the manner in which the explant is removed from the seedlings for culturing by the process of this invention. For optimum results, cotyledonary node along with the axil may be taken out of the seedlings 2–20 days old. However, depending upon the variety and the combination of phytohormones used, maximum number of shoots may be obtained from the explant removed from seedlings of specific age.

According to yet another embodiment of the invention the process can be repeated by using the basal mass left after harvesting the shoots as described in step (vi). The basal mass is cut into 2 to 6 pieces and cultured as in step (iv) and the remaining steps till step (viii) are continued as explained above to obtain the second cycle of shoot proliferation.

The details of the process of the present invention are given below:

To make the seeds free of bacterial/fungal contaminants these are surface sterilized before use. A variety of sterilizing techniques are known for surface sterilization. Such sterilizing methods involve dipping the seeds in a solution containing at least one sterilizing agent. Such sterilizing agents may be any of sodium hypochlorite, calcium hypochlorite, mercuric chloride, alcohol, sulfuric acid etc. The surface sterilization of seeds can be performed by dipping the seeds in 0.05 to 0.5%—w/v solution of mercuric chloride in water for 1 to 15 min with continuous shaking and seeds are then washed thoroughly with deionized distilled water (3–10 times) followed by dipping the seeds in ethanol or rectified spirit (50–100% w/v) for 30 sec to 10 min and flaming.

Surface sterilized seeds can be placed for germination on water containing some gelling agent like agar 0.6 to 1.2% in germination bottles on moistened paper towels or on culture medium containing Murashige and Skoog salts or any other conventional medium, vitamins of B5 medium or other vitamin mixture and any carbon source like glucose or sucrose 1 to 6% w/v and gelling agent like Agar 0.6 to 1.2% w/v or gelrite (phytagel) 0.2 to 0.5% w/v, adjusting pH of medium to 5.6 to 6.2 prior to autoclaving at 121° C. 15 lb/cm for 20 min.

1–2 seeds can be placed in each of 50 ml culture tubes of glass containing 10–15 ml medium for germination or 1–10 seeds can be placed in bigger (250 ml) plastic or glass jar containing 50 ml of the medium. For germination, seeds may be incubated at temperature 20–40° C. in light (at least 40 μmol/m$^2$s) 16 hr photoperiod. Incubation was continued till seed germinates to give radical and plumule with fully expanded cotyledonary leaves.

Cotyledonary node (explant) can preferably be obtained from 2–20 days old seedlings after germination by cutting with a sharp sterile scalpel and blade in an environment free of contaminants i.e., laminar flow known in the art. Cotyledonary node along with axil was excised in such a way that the tissues at the node are not injured.

The cotyledonary node (explant) can be placed in the medium containing salts of Murashige and Skoog at the concentrations as given in table 2 or at half of the concentration on weight by volume basis, vitamins of B5 or of any other vitamin composition, carbon source may be sucrose or glucose 1 to 6% w/v, commonly used growth regulators e.g., cytokinins-BAP (6-benzylaminopurine), 6-benzyladenine, kinetin, zeatin and 2iP (γγDimethyl allylamino purine) etc., and gelling agent agar 0.6 to 1.2% or phytagel (gelrite) 0.2 to 0.5% w/v. The medium is adjusted to pH 5.4 to 6.2 prior to autoclaving at 121° C., 15 lb/cm for 20 min. Composition of the medium provided for shoot proliferation is provided in Table 3.

Cultures are incubated at temperature 20–40° C. in white fluorescent light (40–100 μmol/m$^2$s) 16 h photoperiod, until multiple shoots are formed. This is accompanied by swelling at the basal part of the explant. At this stage, shoots are harvested and transferred to the medium containing Murashige and Skoog salts that may be used at full quantities as mentioned in table 3 or at half the level on weight by volume basis, vitamins of B5 or any other vitamin composition known in the art, carbon source such as glucose or fructose or sucrose at 1 to 6% w/v growth regulators of auxin type for the purpose of root induction e.g., indole acetic acid, naphthalene acetic acid, indole butyric acid (up to 50 μM), gelling agent Agar 0.6 to 1.2% w/v or gelrite 0.2 to 0.5'0-w/v and the medium adjusted to pH 5.6 to 6.2 prior to autoclaving at 121° C., 15 lb/cm for 20 min. Composition of this medium that induces roots is provided in Table 4. The culture was continued till roots developed and shoots grew to give 2 to 4 whorls of leaves.

The remaining basal tissue (after harvesting the shoots) can be divided into parts and can be cultured again in medium as given in Table 3 to give a second cycle of shoot proliferation.

Culturing is continued till multiple shoots are formed. At this stage, the shoots can be harvested again and may be transferred to rooting medium as described in Table 4. The remaining basal mass can again be cultured for next cycle of shoot development. In this way one can harvest up to 30 shoots within 3 cycles of culture, starting with single explant.

Such shoots with well developed roots can be taken out of the culture, washed with sterile distilled water to remove the traces of nutrients present at surface of the roots, followed by keeping the plantlets in some nutrient solution e.g, Hoagland solution (free of sugars) for autotrophic growth. When autotrophic growth starts they may be transferred to vermiculite and finally to soil for development of mature seed bearing plants.

The process of the present invention for inducing high frequency of shoots leads to whole plant development. The basis of the multiplication to obtain multiple shoots from cotyledonary node involves cells other than the original meristems which naturally grow and develop to single plant. We have identified an explant from seedling which gives new meristems resulting in multiple shoots when cultured on medium supplemented with suitable concentration of appropriate growth regulators. The technique can be applied to any variety of cotton. The process is a novel approach and is free of genotypic limitation and also reduces the time required for regeneration of shoots, which are serious problems in the earlier art.

The process of the present invention is directed towards differentiation of shoots from cells other than the pre-existing meristem of the germinated seed. So it is thought that the culture of explant in the presence of suitable concentration of growth regulators results in revising the programmed of cells to produce multiple shoots. The pre existing meristem grows into a single shoot. The new meristems generated by the process reported in this invention give rise to several shoots.

As of now, a detailed process on formation of multiple shoots from any tissue explant of any cultivar of cotton is not available. Reports dealing with tissue culture methods leading to micropropagation are limited to plant regeneration via somatic embryogenesis. Only a few cultivars, namely Coker lines respond successfully to the earlier used process of somatic embryogenesis. Developmental steps in plant regeneration via somatic embryogenesis take several months. Further, the plants obtained by somatic embryogenesis may be morphologically and cytogenetically abnormal and sterile. The present invention describes for the first time a detailed protocol for organogenesis of an explant to give multiple shoots in cotton. With the process of this invention, repeated subculture of explant in the medium supplemented with suitable concentration of growth regulators, produces multiple regeneration of shoots the number of which is significant, ranging from 3 to 30. This result is not suggested in earlier publications and is very significant for the development of multiple plantlets from a single explant.

The following examples are given by way of illustration of the present invention and should not be construed to limit the scope of the present invention.

EXAMPLE-1
Source of Explant and Genotype

Seeds of cotton (*G. hirsutum* c.v. Khandwa-2) plants were surface sterilized by treating with 0.1% mercuric chloride for 7 min. Seeds were then washed with sterile distilled water 5 times, dipped in alcohol (90% v/v) for 30 seconds and flamed. The sterile seeds were placed on the medium containing Murashige and Skoog salts, vitamins of B5, sucrose 3% w/v and agar as gelling agent at 0.8% w/v, pH of medium was adjusted to 5.8 prior to autoclaving. Two seeds were placed in each of 50 ml glass tubes containing 15 ml medium. Seeds were placed with the help of sterile forceps into a microorganism free environment (i.e., laminar flow). Seeds on the medium were incubated at 25±2° C., in white fluorescent light (60 μmol m²s) in 16 h photoperiod till seeds germinate to give radical and plumule with well expanded cotyledonary leaves.

Six day old seedlings were used to cut the explant (small pieces of the seedling which are used for regeneration experiments as starting material). Different types of explants were cut e.g., hypocotyl sections, discs from cotyledonary leaves, mature embryo isolated from seed, immature embryo isolated from immature seed, cotyledonary node (axil), taken without or with one or part of cotyledonary leaf and about 0.5 cm of hypocotyl.

These different explants were placed on the medium consisting of Murashige and Skoog salts, vitamins of B5, glucose 3% w/v, 6-benzyl adenine 22.19 μM and gelling agent agar 0.6% w/v. The pH of the medium was adjusted to 5.8 prior to autoclaving. Culturing was continued to get regeneration of multiple shoots. It was observed that apical meristem taken along with both cotyledonary leaves failed to give multiple shoots. Sections of hypocotyl, cotyledonary leaf and mature as well as immature embryo failed to give multiple shoots. Cotyledonary node taken along with 0.5 cm hypocotyl and one or part of cotyledonary leaf gives multiple shoots on the above medium. The cotyledonary node taken without any cotyledonary leaves also gave large number of shoots in the medium containing 6-benzyl-adenine 8.87 μM and kinetin 9.29 μM.

The identification of the type of cotyledonary nodal explants and the combinations of growth regulators to which these respond are important aspects of this invention.

EXAMPLE 2
Media Dependent Response of Explant

Seeds of cotton (*G. hirsutum* L. Khandwa-2) plants were treated with 0.1% w/v mercuric chloride for 7 min., washed with sterile distilled water 6 times followed by dipping the seeds in alcohol (90% w/v) for 30 sec and flamed. The sterile seeds were placed on the medium containing Murashige and Skoog salts, vitamins of B5, sucrose 3% w/v and agar 0.8% w/v (pH of the medium was adjusted to 5.8 prior to autoclaving). For germination, two seeds were kept in each glass tube containing 15 ml of medium. Seeds on the medium were incubated at, 25±2° C. in white fluorescent light (60 μmol/m²s) 16 hr photoperiod. Seeds were placed onto the medium with the help of sterile forceps under contamination-free environment (Laminar flow). The culture was continued till seeds germinate to give radical and plumule with well expanded cotyledons.

Six day old seedlings were used to provide the seed axil that bears the cotyledonary node (explant). Explant was cut with the help of sharp scalpel. The explant was placed on the medium containing Murashige and Skoog salts, vitamins of B5, glucose and/or sucrose 3% w/v, 6-benzyl adenine 22.19 μM and gelling agent 0.6% w/v (pH of medium was adjusted to 5.8 prior to autoclaving).

Culturing was continued till multiple shoots were formed. Multiple shoots were observed in the presence of 30 g l⁻¹ sucrose or glucose. However, glucose was selected as the preferred carbon source in culture medium based on a comparative study in which glucose, sucrose and glucose plus sucrose were used for multiple shoot differentiation. On media containing sucrose alone or its combination with glucose, a higher amount of phenolics leached out, causing browning in the medium. Phenolics leaching was minimum when glucose was given as the only carbon source. High phenolics in the medium caused reduced growth of shoots and ultimate death of the explant. Use of glucose (in preference to sucrose) for cotton is an important aspect of the invention. It prevents phenolic leaching. The protocol does not require frequent subculture of the growing explant. This has been an important problem in tissue culture of cotton in the previous reports.

Culturing of the cotyledonary node (explant) was also done on the media containing Murashige and Skoog salts, vitamins of B5, glucose 3% w/v, growth regulators at different concentration e.g. BAP (6-benzyl adenine) 2.22 μM to 44.38 μM, KIN (kinetin) 2.32 μM to 44.47 μM and 2iP (γγdimethyl allylamino purine) 2.46 μM to 49.21 μM and combinations of 6-benzyl adenine with dimethyl allylamino purine and kinetin, and gelling agent agar 0.6% w/v (pH of the medium was adjusted to 5.8 prior to autoclaving).

Cultures were incubated at 25±2° C. in white fluorescent light (60 μmol/m²s) 16h photoperiod till multiple shoots were formed. Results obtained are summarized in table 5 and 6.

TABLE 5

Effect of cytokinins on shoot development from explants (cotyledonary node along with one cotyledonary leaf) of cultivar "Khandwa-2" in the first cycle of regeneration.

| Cytokinin (concentration $\mu$M) | Explants forming shoots (%) | Mean number of shoots formed per explant, ±SE (1st Cycle)* | Remarks |
|---|---|---|---|
| BAP (2.22) | 66 | 0.8 ± 0.17 (a) | |
| BAP (4.44) | 73 | 1.23 ± 0.27 (a) | |
| BAP (8.87) | 70 | 2.90 ± 0.57 (b) | |
| BAP (13.31) | 66 | 3.28 ± 0.60 (b) | |
| BAP (22.19) | 80 | 4.46 ± 0.68 (b) | |
| BAP (33.09) | 66 | 3.07 ± 0.65 (b) | poor shoot growth |
| BAP (44.38) | 60 | 3.33 ± 0.49 (b) | poor shoot growth |
| KIN (2.32) | 26 | 0.8 ± 0.2 (a) | |
| KIN (4.65) | 33 | 0.8 ± 0.2 (a) | |
| KIN (9.29) | 26 | 2.00 ± 0.54 (b) | |
| KIN (13.94) | 53 | 2.20 ± 0.41 (b) | |
| KIN (23.23) | 60 | 3.10 ± 0.43 (b) | root formation |
| KIN (34.85) | 60 | 2.00 ± 0.31 (b) | root formation |
| KIN (46.47) | 60 | 2.80 ± 0.48 (b) | root formation |
| 2iP (2.46) | 20 | 0.6 ± 0.24 (a) | |
| 2iP (4.92) | 26 | 0.4 ± 0.16 (a) | |
| 2iP (9.84) | 40 | 0.46 ± 0.16 (a) | |
| 2iP (14.76) | 53 | 0.73 ± 0.52 (a) | |
| 2iP (24.61) | 60 | 1.261 ± 0.53 (a) | callus formation |
| 2iP (36.91) | 30 | 1.25 ± 0.41 (a) | callus formation |
| 2iP (49.21) | 30 | 1.09 ± 0.42 (a) | callus formation |

NOTE:
Data shown are the mean ± SE (standard error) calculated from the results of three independent experiments. The treatments classified as a and b are significantly different between the treatments but not within a treatment, as analysed by Student's t test at > 0.05. BAP (6-benzyladenine), Kin (kinetin) and 2IP ($\gamma\gamma$ dimethyl allylamino purine).

TABLE 6

Combined effect of cytokinins on shoot development in the first cycle from explants (cotyledonary node along with one cotyledonary leaf) of cultivar "Khandwa 2" on modified medium.

| Concentration of different cytokinins ($\mu$M) | | | Explants forming shoots (%) | Mean number of shoots formed per explant ± SD* |
|---|---|---|---|---|
| BA | KIN | 2iP | | |
| 4.44 | 4.65 | — | 50 | 0.75 ± 0.21 (a) |
| 8.87 | 9.29 | — | 33 | 1.00 ± 0.36 (a) |
| 13.31 | 13.94 | — | 66 | 2.13 ± 0.19 (b) |
| 22.19 | 23.23 | — | 86 | 3.86 ± 0.48 (c) |
| 4.44 | 4.65 | 2.46 | 60 | 0.73 ± 0.18 (a) |
| 4.44 | 9.29 | 4.92 | 40 | 1.19 ± 0.34 (a) |
| 4.44 | 13.94 | 9.84 | 50 | 1.28 ± 0.38 (a) |
| 4.44 | 23.23 | 24.61 | 66 | 2.20 ± 0.45 (b) |
| 4.44 | 46.47 | 49.21 | 66 | 2.16 ± 0.27 (b) |

NOTE:
Data shown are the mean ± SE (standard error) calculated from the results of three independent experiments. The treatments classified as a, b and c are significantly different between the treatments but not within the treatments, as analysed by Student's t-test at P > 0.05. BA (6-Benzyl adenine), Kin (kinetin) and 2iP ($\gamma\gamma$ dimethyl allylamino purine)

It is clear from the results that variations in concentration of growth regulator give different response with respect to the development of multiple shoots. This aspect can be utilized for developing the most optimal conditions for regeneration of different varieties of cotton plants.

EXAMPLE 3

Cultivar/Species Dependent Response

Seeds of 13 different cultivars of *G. Hirsutum* L and *C. arboreum* were treated with 0.1% w/v mercuric chloride for 7 min., washed with sterile distilled water 6 times followed by dipping the seeds in alcohol (90% v/v) for 30 seconds and flamed.

Sterile seeds of different cultivars were placed on the medium containing Murashige and Skoog salts vitamins of B5, sucrose 30% w/v and agar 0.8% w/v (pH of the medium was adjusted to 5.8 prior to autoclaving). For germination, two seeds were kept in each glass tube containing 15 ml medium. Seeds on the medium were incubated at 25±2° C. in white fluorescent light (60 $\mu$mol /m$^2$s)16 h photoperiod. Seeds were placed on to the medium with the help of sterile forceps in contamination free environment (Laminar flow). Culture was continued till seeds germinated to give radical and plumule with well expanded cotyledons.

Six day old seedlings were used to provide the cotyledonary node (explant). Explant was cut with the help of sharp scalpel. The explant was placed on the medium containing Murashige and Skoog salts, vitamins of B5, glucose 3% w/v, 6-benzyl adenine 22.19 $\mu$M and gelling agent agar 0.6% w/v (pH of medium was adjusted to 5.8 prior to autoclaving at 121° C. and 15 lb/cm$^2$ for 20 min). Cultures were incubated at 25±2° C. in white fluorescent light (60 $\mu$mol/m$^2$s)16 h photoperiod. Culture was continued till multiple shoots were formed.

At this stage, the shoots were harvested and transferred to the medium containing Murashige and Skoog salts, vitamins of B5, sucrose 3% w/v, growth regulator (naphthalene acetic acid) NAA at 2.69 $\mu$M concentration and gelling agent agar 0.8% w/v (pH of medium was adjusted to 5.3 prior to autoclaving). Results obtained are summarized in table 7.

TABLE 7

Organic potential of cotton cultivars on modified medium containing 22.19 $\mu$M 6-benzyl adenine.

| Cultivar | Explants forming shoots (%) | No. of primary shoots (Ist cycle) per explant 1 ± SE | No. of secondary shoots (IInd cycle) per explant 1 ± SE |
|---|---|---|---|
| *Gossypium hirsutum* cv. Khandwa-2 | 80 | 4.46 ± 0.70 (a) | 5.80 ± 0.91 (a) |
| *G. hirsutim* cv. PKV081 | 66 | 2.10 ± 0.56 (b) | 7.08 ± 0.13 (a) |
| *G. hirsutum* cv. RS810 | 73 | 1.90 ± 044 (b) | 4.66 ± 0.86 (a) |
| *G. hirsutum* cv. Pusa 37 | 90 | 2.70 ± 0.42 (b) | 4.30 ± 0.73 (a) |
| *G. hirsutum* cv. Pusa | 80 | 1.60 ± 0.45 (b) | 3.10 ± 0.70 (b) |
| *G. hirsutum* cv. Stoneville | 70 | 1.40 ± 0.40 (b) | 2.80 ± 0.57 (b) |
| *G. hirsutum* | 70 | 2.40 ± 0.63 (b) | 3.50 ± 0.87 (a) |
| *G. hirsutum* CA-1193 | 60 | 2.10 ± 0.56 (b) | 2.50 ± 0.63 (b) |
| *G. hirsutum* cv. Jurhat | 70 | 1.50 ± 0.44 (b) | ND[3] |
| *G. hirsutum* cv. Sima | 90 | 1.90 ± 0.44 (b) | ND |
| *G. hirsutum* cv. LH1343 | 87 | 2.47 ± 0.37 (b) | ND |
| *G. arboreum* cv. Shyamly | 50 | 1.00 ± 0.39 (b) | 2.20 ± 1.00 (b) |
| *G. arboreum* cv. Lohit | 40 | 0.50 ± 0.16 (c) | 0.90 ± 0.34 (c) |

[1]The data represent mean ± SE (standard error) calculated from the results of three independent experiments taking 10 to 15 replicates each, as described in Methods.
[2]The treatments classified as a, b and c are significantly different between the treatments but not within a treatment, as analysed by statistically test at P > 0.05.
[3]Not done From results in the table it is very clear that the process works for all the thirteen cultivars of cotton. However, species related differences in organogenesis were observed, as cultivars of *G. hirsutum* were more responsive when cultured on the medium containing 22.19 $\mu$M 6-benzyl adenine, while cultivars of *G. arboreum* were less responsive.

Further, when in the first cycle of regeneration, shoots were removed for development of roots, the remaining basal mass of explant was again cultured in the medium for next cycle of regeneration. Regenerants were again harvested and transferred to medium containing suitable concentration of growth regulators for the development of roots and the remaining basal mass was again cultured in the medium for next cycle of regeneration. In this way, we could harvest up to 30 shoots within 3 cycles of culture, starting with a single explant.

According to various aspects of this invention an easy, efficient and reproducible method is provided for inducing a high frequency of direct differentiation of regenerants and plant regeneration from several cultivars of cotton. The process of this invention provides the direct differentiation of shoots and offers many advantages as previously described. The rapidity and high frequency of direct shoot morphogenesis routinely obtainable in cultures by this method, is expected to facilitate genetic transformation of cotton cultivars via *Agrobacterium tumefaciens* and/or biolistic transformation techniques.

What is claimed is:

1. A method for regenerating viable and fertile cotton plants by tissue culture from an apical explant of a germinated cotton seedling, said method comprising the steps of:

(i) cutting from the germinated cotton seedling the apical explant, said explant consisting essentially of a hypocotyl and an apical meristem, (ii) culturing the explant for the purpose of shoot proliferation in a first medium that is free of auxin and sucrose, at a temperature between 20 to 40° C. in light of at least 40 $\mu mol/m^2 s$ for a 16 hour photoperiod, said first medium having a pH in the range of 5.4 to 6.2, being sterile as a result of autoclaving and comprising:
    a. salts,
    b. vitamins,
    c. glucose,
    d. cytokinins at a concentration between 0.1 to 100 $\mu M$, and
    e. a gelling agent;

(iii) continuing culturing of the explant for a minimum period of 4 weeks until shoots are formed;

(iv) harvesting the shoots by removing said shoots from a basal mass of regenerating tissue; and (v) culturing each harvested shoot in a second medium at a temperature between 20 to 40° C. in light of at least 40 $\mu mol/m^2 s$ for a 16 hour photoperiod until roots are formed, said second medium having a pH in the range of 5.4 to 6.2, being sterile as a result of autoclaving, and comprising:
    a. salts,
    b. vitamins,
    c. a carbon source,
    d. auxins at a concentration between 0 to 50 $\mu M$, and
    e. a gelling agent;

wherein viable and fertile cotton plants are obtained.

2. The method according to claim 1, wherein said first and second medium each comprises salts of Murashige and Skoog medium and vitamins of B5 medium.

3. The method according to claim 1, wherein the first and second medium each comprises the following salts of Murashige and Skoog medium:

| Component | Concentration (mg/L) |
|---|---|
| a. Salts of Murashige and Skoog medium: | |
| $NH_4NO_3$ | 1650 |
| $KNO_3$ | 1900 |
| $MgSO_4 7H_2O$ | 370 |
| $MnSO_4 H_2O$ | 169 |
| $ZnSO_4 7H_2O$ | 8.6 |
| $CuSO_4 5H_2O$ | 0.025 |
| $CaCl_2 H_2O$ | 440 |
| KI | 83 |
| $CoCl_2 2H_2O$ | 0.025 |
| $KH_2PO_4$ | 170 |
| $H_3BO_3$ | 6.2 |
| $Na_2MoO_4 2H_2O$ | 0.25 |
| $FeSO_4 7H_2O$ | 27.85 |
| $Na_2EDTA$ | 37.3 |
| Myoinositol | 100. |

4. The method according to claim 3, wherein the salts of Murashige and Skoog medium in the first or second medium is at half the concentration of salts of Murashige and Skoog medium in claim 3.

5. The method according to claim 1, wherein the vitamins of each of the first and second medium comprise:

| Components | Concentration (mg/L) |
|---|---|
| Nicotinic acid | 1.0 |
| Pyridoxine HCl | 1.0 |
| Thiamine HCl | 10.0 |

6. The method according to claim 1, wherein the carbon source of the second medium is selected from the group consisting of sucrose and glucose.

7. The method according to claim 1, wherein the carbon source of each of the first and second medium is present at a range of 1 to 6% wt/vol.

8. The method according to claim 1, wherein the cytokinins of the first medium are selected from the group consisting of 6-benzyl amino purine, 6-benzyl adenine, zeatin, γγdimethyl allylamino purine and kinetin.

9. The method according to claim 1, wherein said explant is isolated from a germinated cotton seedling that is 2 days to several weeks old.

10. The method according to claim 1, wherein the germinated cotton seedling is obtained from a cotton plant grown in a field or by tissue culture.

11. The method according to claim 1, further comprising the steps of culturing the basal mass of regenerating tissue for sustained regeneration of plantlets by a method comprising the steps of:

(i) culturing the basal mass in the first medium, at a temperature between 20 to 40° C. in light of at least 40 $\mu mol/m^2 s$ for a 16 hour photoperiod for the purpose of shoot proliferation, (ii) continuing culturing the basal mass for a minimum period of 4 weeks until shoots are formed;

(iii) harvesting the resulting shoots by removing said shoots from the basal mass; and (iv) culturing each harvested shoot in the second medium at a temperature between 20 to 40° C. in light of at least 40 $\mu mol/m^2 s$ for a 16 hour photoperiod until roots are formed.

12. The method according to any one of claims 1, 3, 5, 10, 11, or 4, wherein the gelling agent is selected from the group consisting of agar and gelrite at a concentration between 0.2 to 1.2% w/v in said first or second medium.

13. The method according to claim 1, wherein the auxins in the second medium are selected from the group consisting of indole acetic acid, indole butyric acid and naphthalene acetic acid.

14. The method according to claim 1, wherein the germinated cotton seedling is obtained by culturing a cotton seed by a process comprising the steps of:
   (i) decontaminating the cotton seed; and
   (ii) culturing the decontaminated cotton seed in a third medium at a temperature between 20 to 40° C. in the presence of light of at least 40 $\mu$mol/m$^2$s for a 16 hour photoperiod for 3 days to several weeks, said third medium having a pH in the range of 5.4 to 6.2, being sterile as result of autoclaving, and comprising:
   a. salts,
   b. vitamins,
   c. a carbon source, and
   d. a gelling agent.

15. The method according to claim 1, wherein the first medium further comprises cytokinin active urea.

16. The method according to claim 15, wherein the cytokinin active urea in the first medium is selected from the group consisting of: 1-phenyl-3-1,2,3 thidiazol-5-yl urea, diphenyl urea and 4-1-phenyl N (4 pyridyl) urea.

17. The method according to claim 14, wherein the third medium comprises the following salts of Murashige and Skoog medium:

| Component | Concentration (mg/L) |
|---|---|
| a. Salts of Murashige and Skoog medium: | |
| NH$_4$NO$_3$ | 1650 |
| KNO$_3$ | 1900 |
| MgSO$_4$7H$_2$O | 370 |
| MnSO$_4$H$_2$O | 169 |
| ZnSO$_4$7H$_2$O | 8.6 |
| CuSO$_4$5H$_2$O | 0.025 |
| CaCl$_2$H$_2$O | 440 |
| KI | 83 |
| CoCl$_2$2H$_2$O | 0.025 |
| KH$_2$PO$_4$ | 170 |
| H$_3$BO$_3$ | 6.2 |
| Na$_2$MoO$_4$2H$_2$O | 0.25 |
| FeSO$_4$7H$_2$O | 27.85 |
| Na$_2$EDTA | 37.3 |
| Myoinositol | 100. |

18. The method according to claim 17, wherein the salts of Murashige and Skoog medium is at half the concentration of the third medium in claim 17.

19. The method according to claim 14, wherein the vitamins of the third medium comprise:

| Component | Concentration (mg/L) |
|---|---|
| Nicotinic acid | 1.0 |
| Pyridoxine HCl | 1.0 |
| Thiamine HCl | 10.0. |

20. The method according to claim 14, wherein said third medium comprises salts of Murashige and Skoog medium and vitamins of B5 medium.

21. The method according to claim 14, wherein the carbon source of the third medium is selected from the group consisting of sucrose and glucose.

22. The method according to claim 14, wherein the carbon source of the third medium is present at a range of 1 to 6% wt/vol.

23. The method according to any one of claims 17, 19 or 18, wherein the gelling agent is selected from the group consisting of agar and gelrite at a concentration between 0.2 to 1.2% w/v in said third medium.

* * * * *